(12) United States Patent
Yamashita et al.

(10) Patent No.: US 9,958,468 B2
(45) Date of Patent: May 1, 2018

(54) AUTOMATIC ANALYZER

(71) Applicant: HITACHI HIGH-TECHNOLOGIES CORPORATION, Tokyo (JP)

(72) Inventors: Yoshihiro Yamashita, Tokyo (JP); Toshiharu Suzuki, Tokyo (JP); Takaaki Hagiwara, Tokyo (JP); Kazunori Yamazawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days. days.

(21) Appl. No.: 14/901,370

(22) PCT Filed: Jul. 25, 2014

(86) PCT No.: PCT/JP2014/069762
§ 371 (c)(1),
(2) Date: Dec. 28, 2015

(87) PCT Pub. No.: WO2015/019880
PCT Pub. Date: Feb. 12, 2015

(65) Prior Publication Data
US 2016/0154016 A1   Jun. 2, 2016

(30) Foreign Application Priority Data

Aug. 9, 2013 (JP) ................................ 2013-166844

(51) Int. Cl.
*G01N 35/00* (2006.01)
*G01N 21/00* (2006.01)
(Continued)

(52) U.S. Cl.
CPC ... *G01N 35/0092* (2013.01); *G01N 35/00712* (2013.01); *G01N 35/00871* (2013.01);
(Continued)

(58) Field of Classification Search
CPC .......... G01N 35/00; G01N 21/00; G01N 1/00; G01N 15/00; G01N 33/00; G01N 33/48; G01N 31/00
(Continued)

(56) References Cited

U.S. PATENT DOCUMENTS

2005/0175506 A1   8/2005  Matsubara et al.
2008/0011106 A1*  1/2008  Kitagawa ............. G01N 35/025
                                                    73/863
(Continued)

FOREIGN PATENT DOCUMENTS

EP          0359049 A2    3/1990
EP       2 372 369 A2    10/2011
(Continued)

OTHER PUBLICATIONS

International Search Report of PCT/JP2014/069762.
(Continued)

*Primary Examiner* — Brian J. Sines
(74) *Attorney, Agent, or Firm* — Mattingly & Malur, PC

(57) ABSTRACT

The present invention provides an automatic analyzer capable of reducing the time necessary for analysis processing by making various operations pertaining to the analysis processing more efficient. More specifically, the present invention is characterized in that, from among a plurality of ending operation items set as analysis ending operations to perform at the end of analysis operations for analyzing a sample under analysis, one or more ending operation items to be performed are selected, and on the basis of monitoring results of monitoring the status of an automatic analyzer during the period from the end of the analysis ending operations to the start of analysis preparation operations for preparing for the analysis operations, one or more preparation operation items to be performed are selected from
(Continued)

among a plurality of preparation operation items set as analysis preparation operations.

5 Claims, 4 Drawing Sheets

(51) Int. Cl.
    *G01N 1/00*         (2006.01)
    *G01N 15/00*      (2006.01)
    *G01N 33/00*      (2006.01)
    *G01N 33/48*      (2006.01)
    *G01N 31/00*      (2006.01)

(52) U.S. Cl.
    CPC ............. *G01N 2035/0091* (2013.01); *G01N 2035/0094* (2013.01); *G01N 2035/00643* (2013.01); *G01N 2035/00673* (2013.01)

(58) Field of Classification Search
    USPC ............ 422/50, 68.1, 62, 63, 82.01, 82.05; 436/43, 164, 174
    See application file for complete search history.

(56) References Cited

U.S. PATENT DOCUMENTS

| | | | | |
|---|---|---|---|---|
| 2008/0056939 A1* | 3/2008 | Awata | ............. | G01N 35/00663 422/50 |
| 2008/0279048 A1* | 11/2008 | Wakamiya | ....... | G01N 35/00663 368/10 |
| 2009/0117620 A1* | 5/2009 | Fritchie | ................ | B01L 3/5085 435/91.1 |
| 2010/0115463 A1* | 5/2010 | Kondou | ................ | B01L 3/527 715/803 |
| 2012/0251391 A1 | 10/2012 | Hagiwara et al. | | |
| 2014/0147335 A1* | 5/2014 | Sarwar | ............ | G01N 35/00722 422/63 |
| 2015/0212102 A1 | 7/2015 | Hagiwara et al. | | |
| 2015/0316569 A1* | 11/2015 | Fujita | ............... | G01N 35/00584 422/67 |

FOREIGN PATENT DOCUMENTS

| | | |
|---|---|---|
| JP | 01-284760 A | 11/1989 |
| JP | 01-288768 A | 11/1989 |
| JP | 02-80962 A | 3/1990 |
| JP | 6-160397 A | 6/1994 |
| JP | 07-209306 A | 8/1995 |
| JP | 08-338846 A | 12/1996 |
| JP | 10-232234 A | 9/1998 |
| JP | 2004-28932 A | 1/2004 |
| JP | 2009-036723 A | 2/2009 |
| JP | 2009-270940 A | 11/2009 |
| JP | 2010-286410 A | 12/2010 |
| JP | 2011-179825 A | 9/2011 |
| WO | 2010/143397 A1 | 12/2010 |
| WO | 2011/078118 A1 | 6/2011 |

OTHER PUBLICATIONS

International Preliminary Report on Patentability received in corresponding International Application No. PCT/JP2014/069762 dated Feb. 18, 2016.
Extended European Search Report received in corresponding European Application No. 14834229.8 dated Mar. 10, 2017.

\* cited by examiner

[FIG. 1]
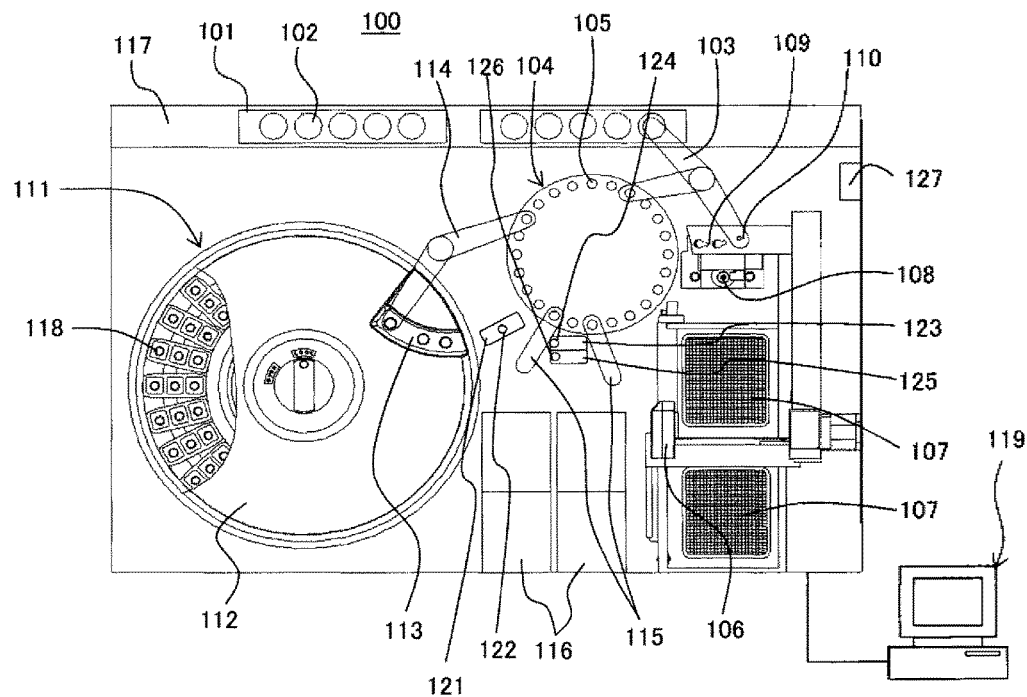
[FIG. 2]
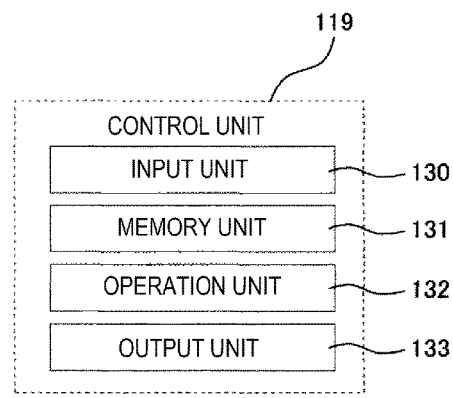

[FIG. 3]
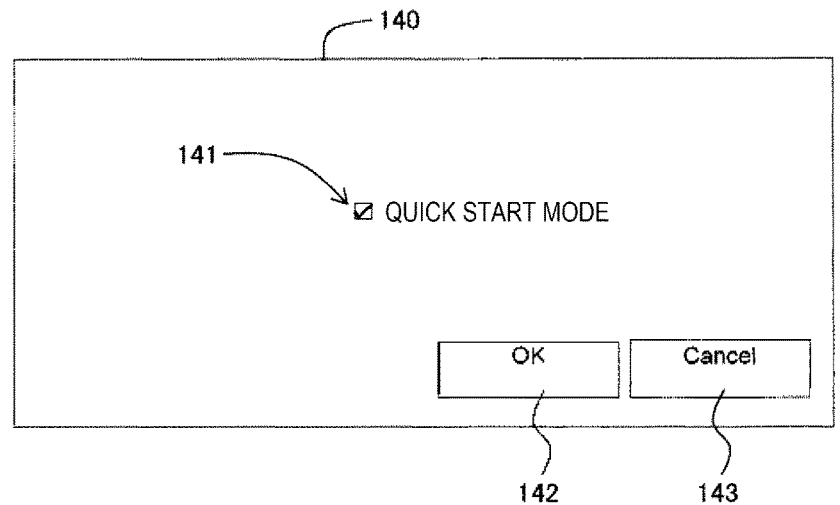
[FIG. 4]
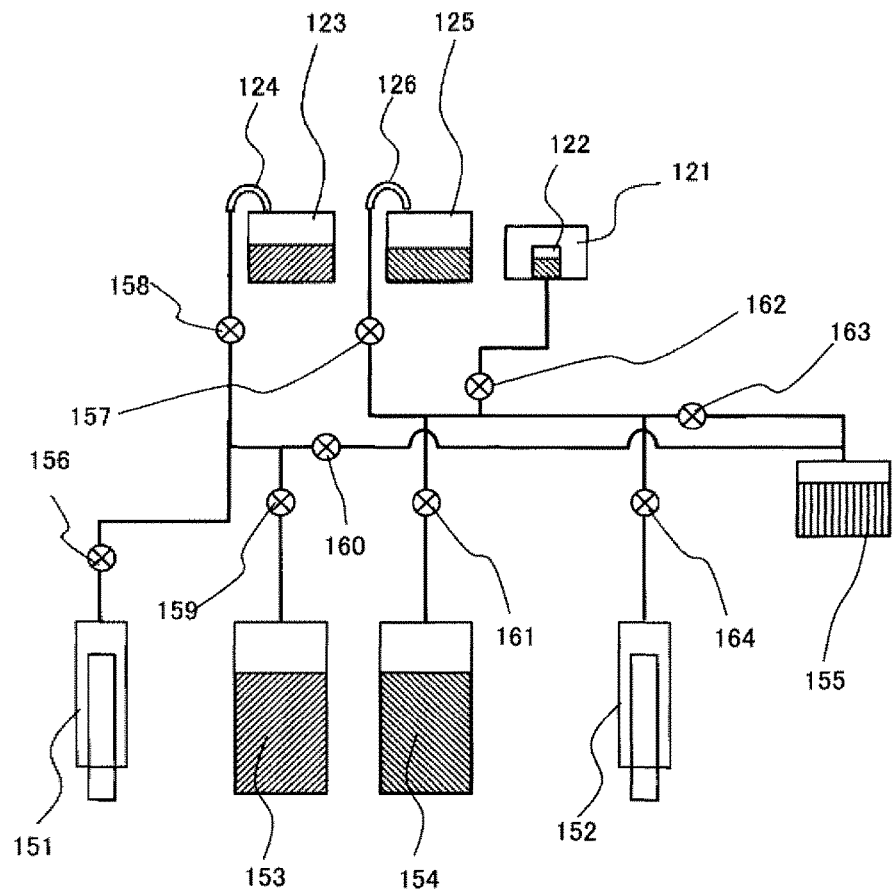

[FIG. 5]
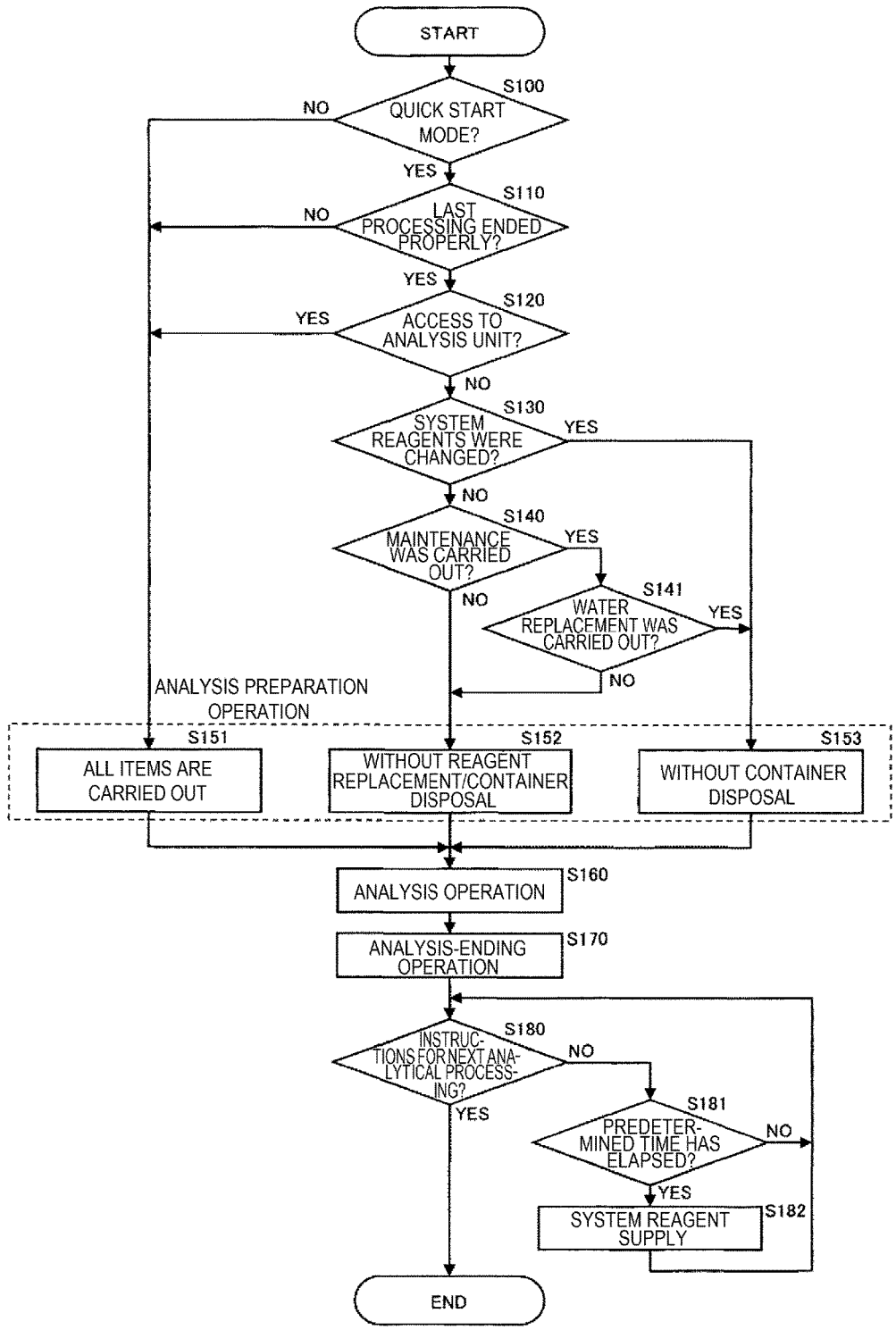

[FIG. 6]
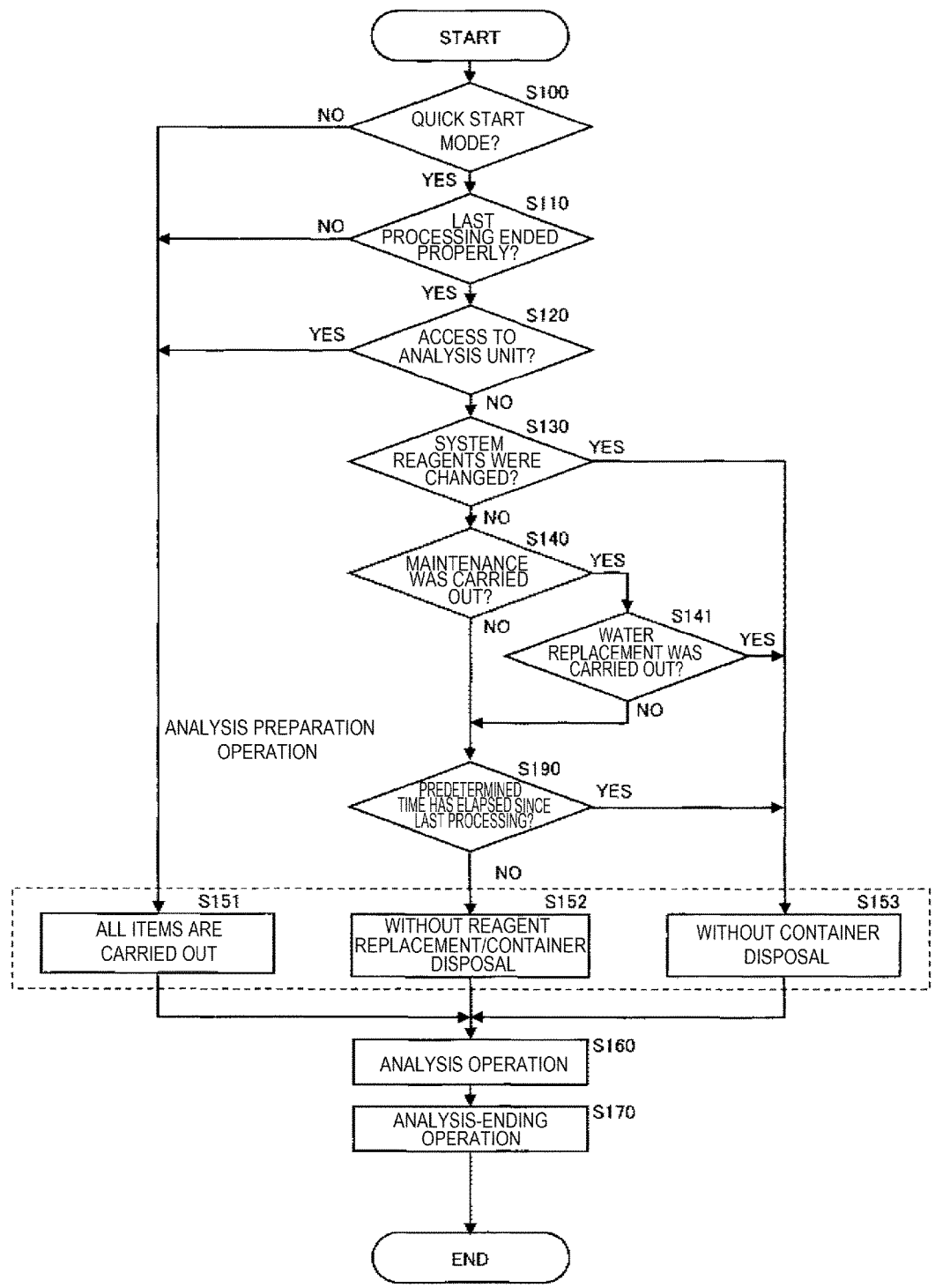

AUTOMATIC ANALYZER

TECHNICAL FIELD

The present invention is related to an automatic analyzer for carrying out the component analysis of a biological sample such as plasma, serum and urine.

BACKGROUND ART

In an automatic analyzer, a reagent which specifically reacts with a specific component contained in a biological sample such as serum, plasma and urine (hereinafter simply referred to as a sample) is added and reacted, and transmitted light or scattered light and chemiluminescence or electrochemiluminescence are measured to carry out quantitative/qualitative analysis of the specific component of the sample.

In such an automatic analyzer, the reliability of the analysis results is improved and the accuracy of the analysis is stabilized by appropriately managing the condition of the analyzer according to circumstances, for example by carrying out a preparation operation for bringing the condition of the analyzer into suitable condition for the analysis before the analysis operation, carrying out an ending operation for bringing the analyzer into proper standby condition after the analysis operation and the like.

Here, the operations which are carried out before and after the analysis operation are related to the increase and the decrease in the TAT (Turn Around Time). Accordingly, for example, for the purpose of shortening the TAT, PTL 1 (WO2011/078118) discloses a technique related to an automatic analyzer in which it is selected whether a designated preparation operation of the analysis preparation processes which are necessary before starting the analysis with the automatic analyzer is carried out during the initial processing for starting up the power supply of the analyzer or after starting the analysis.

CITATION LIST

Patent Literature

PTL 1: WO2011/078118

SUMMARY OF INVENTION

Technical Problem

However, in the conventional technique, by carrying out a designated preparation operation of the analysis preparation processes of the automatic analyzer during the initial processing for starting up the power supply of the analyzer, the period between the point at which the request for analysis is made and the point at which the analysis is actually started is shortened. Thus, the reduction in the TAT is just restricted to the examination soon after starting the analysis, and the technique has room for further improvement.

The invention has been made in view of the above circumstances and aims to provide an automatic analyzer which can shorten the time required for analytical processing by improving the efficiency of the operations related to the analytical processing.

Solution to Problem

In order to achieve the aim, the invention includes an analyzer condition monitoring unit for monitoring the condition of the automatic analyzer between the completion of starting processing of the analyzer and the start of an analysis preparation operation for preparing for an analysis operation and between the completion of an analysis-ending operation and the start of the analysis preparation operation for preparing for the analysis operation and an analysis preparation operation item determining unit for determining one or more preparation operation items to be carried out from preparation operation items set as the analysis preparation operation based on the monitoring result of the analyzer condition monitoring unit.

Advantageous Effects of Invention

According to the invention, the time required for the analytical processing can be shortened by making the operations related to the analytical processing more efficient.

BRIEF DESCRIPTION OF DRAWINGS

FIG. 1 A figure which schematically illustrates the general structure of the automatic analyzer according to an embodiment of the invention.

FIG. 2 A functional block diagram which explains the summary of the control unit.

FIG. 3 A figure which shows an example of the analysis mode selection screen which is one of the setting screens displayed on the output unit.

FIG. 4 A figure which schematically illustrates the flow path structure related to the system reagents of the automatic analyzer according to an embodiment of the invention.

FIG. 5 A flowchart which shows the overall flow of the analytical processing of an embodiment of the invention (example 1).

FIG. 6 A flowchart which shows the overall flow of the analytical processing of an embodiment of the invention (example 2).

DESCRIPTION OF EMBODIMENTS

An embodiment of the invention is explained referring to the drawings.

(1) General Structure

FIG. 1 is a figure which schematically illustrates the general structure of the automatic analyzer according to the embodiment. FIG. 4 is a figure which schematically illustrates the flow path structure related to the system reagents.

In FIG. 1 and FIG. 4, an automatic analyzer 100 is roughly composed of sample containers 102 which contain a sample, a rack 101 which holds the sample containers 102, a rack-carrying line 117 which carries the rack 101, an incubator disk 104 which holds reaction containers 105, a sample dispensing nozzle 103 which dispenses the sample from the sample containers 102 to the reaction containers 105, reagent containers 118 which contain a reagent, a reagent disk 111 which holds the reagent containers 118, a reagent dispensing nozzle 114 which dispenses the reagent from the reagent containers 118 to the reaction containers 105, a reagent dispensing nozzle washing tank 121 for washing the reagent dispensing nozzle 114, a washing reagent supply hole 122 which supplies the reagent nozzle washing tank 121 with a washing reagent, a stirring mechanism 108 which stirs a mixture of the sample and the reagent (hereinafter referred to as a reaction solution) contained in the reaction containers 105, a detection unit 116 which detects a specific component from the reaction solution, a reaction solution suction nozzle 115 which sucks the reaction solution from the reaction containers 105 and sends the reaction solution to the detection unit 116, a detection reaction auxiliary reagent reservoir 123 which holds a detection reaction auxiliary reagent which is sucked by the reaction solution suction nozzle, a detection reaction auxiliary reagent supply nozzle 124 which supplies the detection reaction auxiliary reagent to the detection reaction auxiliary reagent reservoir 123, a washing reagent reservoir 125 which holds the washing reagent which is sucked by the reaction solution suction nozzle, a washing reagent supply nozzle 126 which supplies the washing reagent to the washing reagent reservoir 125, a sensor 127 for detecting opening and closing of a top cover covering an analysis unit and a control unit 119 which controls the operations of the whole automatic analyzer. In addition, in the automatic analyzer 100, a sample dispensing tip-/reaction container-carrying mechanism 106, a sample dispensing tip-/reaction container-holding unit 107, a sample dispensing tip-/reaction container-disposal hole 109 and a sample dispensing tip-attaching unit 110 are provided.

(1-1) Rack-Carrying Line 117

The sample containers 102 are held by the rack 101 and carried along the rack-carrying line 117. The sample containers 102 contain a biological sample to be analyzed such as plasma, serum and urine (hereinafter referred to as a sample). A sample dispensing position is provided on the rack-carrying line 117.

(1-2) Reagent Disk 111

The reagent containers 118 which contain a reagent used for the analytical processing are aligned circumferentially in the reagent disk 111. The reagent disk 111 is driven rotationally in the circumferential direction by a rotational driving device, which is not shown in the drawings, and thus carries the reagent containers 118 in the circumferential direction.

The internal space of the reagent disk 111 in which the reagent containers 118 are held is partitioned off by a reagent disk cover 112 and maintained at a predetermined temperature. The reagent disk cover 112 has a reagent disk cover opening 113 through which the reagent dispensing nozzle 114 accesses the reagent containers 118.

(1-3) Incubator Disk 104

The reaction containers 105 which contain a mixture of the sample and the reagent (a reaction solution) are aligned circumferentially on the incubator disk 104. The incubator disk 104 is driven rotationally in the circumferential direction by a rotational driving device, which is not shown in the drawings, and thus carries the reaction containers 105 in the circumferential direction. On the path on which the reaction containers 105 are carried by the incubator disk 104, a reaction container-setting position, a reagent dispensing position, a sample dispensing position, a detection position, a reaction container disposal position and the like are provided.

(1-4) Sample Dispensing Nozzle 103 and Reagent Dispensing Nozzle 114

The sample dispensing nozzle 103 and the reagent dispensing nozzle 114 are designed in such a manner that the nozzles can rotate horizontally and move up and down. The nozzle tips touch the reagent/diluted solution in a reagent container 118 or the sample in a sample container 102 to suck predetermined amounts, and the reagent/diluted solution and the sample are discharged into a reaction container 105 on the incubator disk 104.

The sample dispensing nozzle 103 dispenses the sample from a sample container 102 which has been carried to the sample dispensing position on the rack-carrying line 117 into a reaction container 105 which has been carried to the sample dispensing position on the incubator disk 104. Before the sample is dispensed, the sample dispensing nozzle 103 moves to above the sample dispensing tip-attaching position 110 and moves down, and a sample dispensing tip is attached to the tip of the sample dispensing nozzle 103. After the sample is dispensed, the sample dispensing nozzle 103 moves to above the sample dispensing tip- and reaction container-disposal hole 109, and the used sample dispensing tip is disposed of into the sample dispensing tip- and reaction container-disposal hole 109.

In the reagent dispensing nozzle washing tank 121 for washing the reagent dispensing nozzle 114, the reagent dispensing nozzle 114 washes the inside of the reagent dispensing nozzle and the outer surface of its tip by sucking and discharging a predetermined amount of the washing reagent which is supplied to the washing reagent supply hole 122 and then dispenses the reagent from a reagent container 118 which has been carried to the reagent dispensing position corresponding to the reagent disk cover opening 113 in the reagent disk 111 to a reaction container 105 which has been carried to the reagent dispensing position on the incubator disk 104. In this regard, the washing reagent is sucked from a washing reagent bottle 154 by a washing reagent supply syringe 152 which is connected through a flow path and changeover valves 161, 162 and 164 and discharged into the washing reagent supply hole 122.

(1-5) Sample Dispensing Tip-/Reaction Container-Holding Unit 107

The sample dispensing tip-/reaction container-holding unit 107 holds unused sample dispensing tips which are to be attached to the tip of the sample dispensing nozzle 103 and unused reaction containers 105 which are to be set on the incubator disk 104.

(1-6) Sample Dispensing Tip-/Reaction Container-Carrying Mechanism 106

The sample dispensing tip-/reaction container-carrying mechanism 106 is designed in such a manner that the sample dispensing tip-/reaction container-carrying mechanism 106 can move in the three directions along X-axis, Y-axis and Z-axis. The sample dispensing tip-/reaction container-carrying mechanism 106 carries the sample dispensing tips from the sample dispensing tip-/reaction container-holding unit 107 to the sample dispensing tip-attaching position 110 and carries the reaction containers 105 to the incubator disk 104. Also, the sample dispensing tip-/reaction container-carrying mechanism 106 carries a reaction container 105 to which the sample and the reagent have been dispensed from the incubator disk 104 to the stirring mechanism 108, and the mixture (the reaction solution) contained in the reaction container 105 is stirred. In other words, the sample dispensing tip- and reaction container-carrying mechanism 106 moves to above the sample dispensing tip- and reaction container-holding member 107, moves down to hold an unused reaction container 105, moves up, moves to above the reaction container-setting position on the incubator disk 104 and moves down to set the reaction container. Also, the sample dispensing tip-/reaction container-carrying mechanism 106 carries the used reaction containers 105 to the sample dispensing tip-/reaction container-disposal hole 109 and disposes of the used reaction containers 105.

(1-7) Reaction Solution Suction Nozzle 115 and Detection Unit 116

The reaction solution suction nozzle 115 can rotate horizontally and move up and down. The reaction solution suction nozzle 115 moves to a reaction container 105 after the reaction on the incubator disk 104, sucks the reaction solution in the reaction container 105 and sends the reaction solution to the detection unit 116 which is connected through a flow path. Also, the reaction solution suction nozzle 115 moves to the detection reaction auxiliary reagent reservoir 123, sucks the detection reaction auxiliary reagent and sends the reagent to the detection unit 116. The detection reaction auxiliary reagent is sucked from a detection reaction auxiliary reagent bottle 153 by a detection reaction auxiliary reagent supply syringe 151 which is connected through a flow path and changeover valves 156, 158, 159 and 160, discharged from the detection reaction auxiliary reagent supply nozzle 124 and stored in the detection reaction auxiliary reagent reservoir. Similarly, the reaction solution suction nozzle 115 moves to the washing reagent reservoir 125, sucks the washing reagent and sends the washing reagent to the detection unit 116. The washing reagent is sucked from the washing reagent bottle 154 by the washing reagent supply syringe 152 which is connected through a flow path and changeover valves 157, 161, 163 and 164, discharged from the washing reagent supply nozzle 126 and stored in the washing reagent reservoir 125.

(1-8) Control Unit 119

FIG. 2 is a functional block diagram which explains the summary of the control unit.

In FIG. 2, the control unit 119 has an input unit 130, a memory unit 131, an operation unit 132 and an output unit 133.

(1-8. 1) Operation Unit 132

The operation unit 132 carries out an analysis preparation operation (described below) which is an operation for bringing the condition of the analyzer into suitable condition for the analysis before carrying out an analysis operation, an analysis operation (described below) for analyzing the sample to be analyzed based on the detection results of the detection unit 116, an analysis-ending operation (described below) for bringing the analyzer into proper standby condition after carrying out the analysis operation and the like, and the operation unit 132 outputs the analysis results and the like to the output unit 133 and stores the analysis results and the like in the memory unit 131 at the same time.

Also, the operation unit 132 has a function as an analyzer condition monitoring unit for monitoring the condition of the automatic analyzer between the completion of a starting processing of the analyzer and the start of the analysis preparation operation for preparing for the analysis operation and between the completion of the analysis-ending operation and the analysis preparation operation and a function as an analysis preparation operation item determining unit for determining one or more preparation operation items to be carried out from preparation operation items set as the analysis preparation operation based on the monitoring results.

Here, the condition of the automatic analyzer which the operation unit 132 monitors by the function as the analyzer condition monitoring unit includes presence or absence of a malfunction during the starting processing of the analyzer, presence or absence of maintenance which is carried out after starting the analyzer and the kind of the maintenance item, presence or absence of access by an operator to the analysis unit, presence or absence of change of the system reagent bottles and the like. The operation unit 132 monitors information on the alarm during the starting processing with respect to the presence or the absence of a malfunction during the starting processing of the analyzer, on the record of the maintenance item which the operator has selected from the operation screen with respect to the maintenance carried out, on the condition of a sensor which detects the opening and closing of the top cover covering the analysis unit with respect to the presence or the absence of the access by the operator to the analysis unit and on the input signal of a bottle change completion button pushed by the operator with respect to the presence or the absence of change of the system reagent bottles. The information is sent to the control unit 119 from each unit of the automatic analyzer and stored in the memory unit 131 and the like.

(1-8. 2) Memory Unit 131

The memory unit 131 stores information regarding the automatic analyzer, such as the detection results of the detection unit 116, the results of the analytical processing computed from the detection results, the settings of the analysis mode (described below) and the like, the passwords which are set for the respective operators, the display level of the screen, the sample information, the reagent information, the analysis parameters, the requested analysis items and the calibration results.

(1-8. 3) Output Unit 133 and Input Unit 130

The output unit 133 is composed of for example a display such as a monitor, a printer and the like, and the output unit 133 displays or prints out the analysis results of the sample and the contents of the settings. The input unit 130 is composed of for example an operation device such as a keyboard and a mouse and carries out various operations through GUI (Graphical User Interface) including setting screens and the like displayed on the monitor or the like of the output unit 133.

FIG. 3 is a figure which shows an example of the analysis mode selection screen which is one of the setting screens displayed on the output unit 133.

In FIG. 3, an analysis mode selection screen 140 has a checkbox 141 for selecting a quick start mode as the analysis mode, an OK button 142 for confirming the content of the setting in the checkbox 141 and a cancel button 143 for cancellation.

The analysis mode selection screen 140 is a setting screen for setting the analysis mode of the automatic analyzer from a normal mode and a quick start mode. The normal mode is a mode for carrying out all of the operation items which are prepared for each of the analysis-ending operation and the analysis preparation operation. In the quick start mode (described in detail below), items which are carried out and items which are not carried out are selected from the operation items of the analysis-ending operation and the analysis preparation operation according to circumstances, and the items are carried out. Thus, the quick start mode is a mode which shortens the time required for the operations by optimizing the analysis-ending operation and the analysis preparation operation and which shortens the time of the analytical processing.

(2) Analysis Preparation Operation, Analysis Operation and Analysis-Ending Operation The details of the analysis preparation operation, the analysis operation and the analysis-ending operation of the embodiment are explained.

(2-1) Analysis Preparation Operation

The analysis preparation operation is an operation for bringing the condition of the analyzer into suitable condition for the analysis before carrying out the analysis operation. In the analysis preparation operation, operation items (hereinafter referred to as preparation operation items) are prepared in advance, and some or all of the operation items are selected from the preparation operation items and carried out. Examples of the preparation operation items include replacement with the system reagents such as the detection reaction auxiliary reagent and the washing reagent, disposal of the reaction containers, removal of bubbles in the flow paths, checking of the functions of the detection sensor and the like. In this regard, of the preparation operation items, the system reagent replacement and the disposal of the reaction containers take relatively long time, and thus the time-shortening effect achieved by optimization thereof is relatively large.

(2-1. 1) System Reagent Replacement

The system reagent replacement is an operation item for replacing the insides of the detection reaction auxiliary reagent reservoir 123, the flow path which connects the detection reaction auxiliary reagent supply nozzle 124 and the detection reaction auxiliary reagent bottle 153, the washing reagent reservoir 125, the flow path which connects the washing reagent supply nozzle 126 and the washing reagent bottle 154, the reagent dispensing nozzle washing tank 121 and the flow path which connects the washing reagent supply hole 122 and the washing reagent bottle 154 with the detection reaction auxiliary reagent or the washing reagent.

During the system reagent replacement, the system reagents, namely the detection reaction auxiliary reagent and the washing reagent, are charged into the system reagent supply nozzles and the system reagent reservoirs from the system reagent bottles, and thus preparation for the detection step is carried out. Also, the washing reagent is supplied to the reagent dispensing nozzle washing tank from the washing reagent bottle, and thus preparation for the reagent dispensing step is carried out.

The system reagent replacement is characterized in that the time required is the longest among the operation items of the analysis preparation operation, because the solutions remaining in the system reagent supply nozzles, the system reagent reservoirs and the reagent probe washing tank are replaced with the system reagents which are supplied from the system reagent bottles of the detection reaction auxiliary reagent and the washing reagent and because the system reagents have to be supplied more than once in amounts corresponding to the total volumes of the flow paths and the reservoirs and the washing reagent supply hole of the reagent probe washing tank.

(2-1. 2) Disposal of Reaction Containers

The disposal of the reaction containers is an operation item for disposing of the reaction containers 105 which remain on the incubator disk 104 and in the stirring mechanism 108.

During the disposal of the reaction containers, it is checked whether there are reaction containers 105 remaining on the incubator disk 104 and in the stirring mechanism 108, and the disposal operation is carried out.

The disposal of the reaction containers is characterized by requiring the second longest time after the system reagent replacement among the operation items of the analysis preparation operation, because when reaction containers 105 remain on the incubator disk 104 and in the stirring mechanism 108, the reaction containers 105 are carried one by one to the sample dispensing tip- and reaction container-disposal hole by the sample dispensing tip- and reaction container-carrying mechanism 106 and disposed of.

(2-1. 3) Removal of Bubbles in Flow Paths

The removal of bubbles in the flow paths is an operation item for removing bubbles in the flow paths of the reagent dispensing nozzle 114 and the sample dispensing nozzle 103.

During the removal of bubbles in the flow paths, system water is discharged from the syringes of the reagent dispensing nozzle 114 and the sample dispensing nozzle 103 to the respective dispensing nozzles through the flow paths. Thus, bubbles in the syringes and the flow paths are removed, and the dispensing accuracy is secured.

(2-1. 4) Checking of Functions of Detection Sensor

The checking of the functions of the detection sensor is an operation item for checking the functions of the detection sensor in the detection unit 116.

During the checking of bubbles of the detection sensor, the condition of the detection sensor is checked using the system reagent (the detection reaction auxiliary reagent), and presence or absence of a malfunction of the detection sensor is checked in advance before carrying out the analysis.

(2-2) Analysis Operation

In the analysis operation, the sample to be analyzed is analyzed by the following steps.

(2-2. 1) Sample Dispensing Processing/Reagent Dispensing Processing

The reagent containers 118 which contain the reagent or a diluted solution are carried to the reagent dispensing position, where the reagent is dispensed by the reagent dispensing nozzle 114, by the rotation of the reagent disk ill. Of the reaction containers 105 which are aligned circumferentially on the incubator disk 104, the reaction container 105 which is used for the analysis operation is carried to the reagent dispensing position by the rotation of the incubator disk 104. At the reagent dispensing position, the reagent in a reagent container 118 is sucked by the reagent dispensing nozzle 114 and discharged into the reaction container 105.

The sample containers 102 which contain a sample to be analyzed are installed in the rack 101 and carried to the sample dispensing position, where the sample is dispensed by the sample dispensing nozzle 103, by the rack-carrying line 117. Of the reaction containers 105 which are aligned circumferentially on the incubator disk 104, the reaction container 105 which is used for the analysis operation is carried to the sample dispensing position by the rotation of the incubator disk 104. At the sample dispensing position, the sample in a sample container 102 is sucked by the sample dispensing nozzle 103 and discharged into the reaction container 105.

(2-2. 2) Stirring Processing

The reaction container 105 into which the sample and the reagent have been discharged is moved to the reaction container-carrying position by the rotation of the incubator disk 104 and carried to the stirring mechanism 108 by the sample dispensing tip- and reaction container-carrying mechanism 106. In the stirring mechanism 108, rotary motion is applied to the reaction container 102 to mix (stir) the sample and the reagent in the reaction container. After finishing stirring, the reaction container 102 is returned to the reaction container-carrying position on the incubator disk 104 by the sample dispensing tip- and reaction container-carrying mechanism 106.

(2-2. 3) Detection Processing

After the reagent and the sample have been dispensed and mixed and a predetermined period has elapsed on the incubator disk 104, the reaction container 105 is carried to the detection position. At the detection position, the reaction solution contained in the reaction container 105 is sucked by the reaction solution suction nozzle 115, and then the detection reaction auxiliary reagent contained in the detection reaction auxiliary reagent reservoir 123 is sucked. The reaction solution and the detection reaction auxiliary reagent are sent to the detection unit 116. The component to be measured is detected from the reaction solution which has been sent to the detection unit 116, and the detection results are sent to the control unit 119. Then, the washing reagent filled in the washing reagent reservoir 125 is sucked and sent to the detection unit 116, and the detection unit 116 is washed. After the system reagents (the detection reaction auxiliary reagent and the washing reagent) in the system reagent reservoirs have been sucked, the system reagents are supplied from the system reagent supply nozzles.

(2-3) Analysis-Ending Operation

The analysis-ending operation is an operation for bringing the analyzer into proper standby condition after carrying out the analysis operation. In the analysis-ending operation, operation items (hereinafter referred to as ending operation items) are prepared in advance, and some or all of the operation items are selected from the ending operation items and carried out. Examples of the ending operation items include replacement of the system reagents with water, disposal of the reaction containers and the like.

(2-3. 1) Replacement of System Reagents with Water

The replacement of the system reagents with water is an operation item for replacing the system reagents in the flow paths of the system reagent supply nozzles, the system reagent reservoirs and the washing reagent supply hole of the reagent probe washing tank with water.

During the replacement of the system reagents with water, the system reagents, namely the detection reaction auxiliary reagent and the washing reagent, in the system reagent supply nozzles, the system reagent reservoirs and the washing reagent supply hole of the reagent probe washing tank are replaced with water. This prevents the precipitation of crystals due to the evaporation and the concentration of the reagents in the system reagent supply nozzles, the system reagent reservoirs and the washing reagent supply hole of the reagent probe washing tank or the deterioration of the reagents during a long period of standby condition.

(2-3. 2) Disposal of Reaction Containers

The disposal of the reaction containers is an operation item for disposing of the reaction containers 105 which remain on the incubator disk 104 and in the stirring mechanism 108.

During the disposal of the reaction containers, a reaction container 105 from which the reaction solution has been sucked is carried to the reaction container disposal position by the rotation of the incubator disk 104, carried to above the sample dispensing tip- and reaction container-disposal hole 109 from the incubator disk 105 by the sample dispensing tip- and reaction container-carrying mechanism 106 and disposed of through the sample dispensing tip- and reaction container-disposal hole 109.

(3) Analytical Processing

FIG. 5 and FIG. 6 are flowcharts which show the overall flow of the analytical processing of the embodiment.

In FIG. 5, when the input unit 130 or the like instructs to start the analytical processing, the control unit 119 decides whether the setting of the analysis mode is the quick start mode (a step S100) and, when the decision result is NO, all of the items of the analysis preparation operation are carried out (a step S151).

When the decision result in the step S100 is YES, it is decided whether the last analytical processing (or the starting processing of the automatic analyzer) has been ended properly (a step S110). When the decision result is YES, then it is decided whether the operator has accessed the analysis unit (the incubator disk 104, the reservoirs and the like) to carry out any operation after the completion of the analysis-ending operation of the last analytical processing (or the starting processing of the automatic analyzer) based on the monitoring of the condition of the opening/closing sensor of the analysis unit top cover (a step S120). When the decision result in the step S110 is NO or when the decision result in the step S120 is YES, all of the items of the analysis preparation operation are carried out (a step S151).

When the decision result in the step S120 is NO, it is decided whether the system reagent bottles have been changed (a step S130). When the decision result is YES, the item of the disposal of the reaction containers in the analysis preparation operation is not carried out, that is, the items except for the disposal of the reaction containers are carried out (a step S153).

When the decision result in the step S130 is NO, it is decided whether maintenance has been carried out (a step S140), and when the decision result is YES, it is decided whether the system reagents have been replaced with water (a step S141). When the decision results in both of the steps S140 and S141 are NO, the items of the system reagent replacement and the disposal of the reaction containers in the analysis preparation operation are not carried out, that is, the items except for the items of the system reagent replacement and the disposal of the reaction containers are carried out (a step S152).

When the decision result in the step S141 is YES, the item of the disposal of the reaction containers in the analysis preparation operation is not carried out, that is, the items except for the disposal of the reaction containers are carried out (the step S153).

When the analysis preparation operation (the step S151, S152 or S153) finishes, the analysis operation is then carried out (a step S160), and, of the operation items of the analysis-ending operation, the operation items according to the setting of the analysis mode are carried out as the analysis-ending operation (a step S170).

Then, it is decided whether instructions to carry out the next analytical processing have been given (a step S180). It is decided whether a predetermined time elapsed since the analysis-ending operation (the step S170) (a step S181) when the decision result is NO, while when the decision result is YES, the system reagents are supplied (a step S182) and the step S180 is carried out again. When the decision result in the step S181 is NO, the step S180 is carried out again without carrying out anything.

When the decision result in the step S180 is YES, the processing is finished, and the next analytical processing is carried out.

In the flowchart of FIG. 6, after the decision in the step S140 or the step S141 is made, it is decided whether the elapsed time since the completion of the last analysis or the elapsed time since a maintenance operation which has been carried out for replacing or supplying the system reagents is a certain time or longer (a step S190). When the decision result is YES, the item of the disposal of the reaction containers in the analysis preparation operation is not carried out, that is, the items except for the disposal of the reaction containers are carried out (the step S153). When the decision result is NO, the items of the system reagent replacement and the disposal of the reaction containers in the analysis preparation operation are not carried out, that is, the items except for the items of the system reagent replacement and the disposal of the reaction containers are carried out (the step S152). In this regard, the step S190 is for preventing the evaporation and the deterioration of the system reagents caused when a certain period of time elapses from the last processing and is regarded as an alternative to the steps S180, 181 and 182 shown in FIG. 5.

(4) Operations

The operations of the embodiment designed as explained above are explained.

While the analytical processing is carried out, when there has been no malfunction during the starting processing of the analyzer, no maintenance carried out after the starting processing of the analyzer, no access by the operator to the analysis unit and no change of the system reagent bottles, it is decided that the insides of the flow paths of the system reagent supply nozzles, the system reagent reservoirs and the washing reagent supply hole of the reagent nozzle washing tank have already been replaced with the system reagents and that no reaction container 105 remains on the incubator disk 104 and in the stirring mechanism 108. Then, from the analysis preparation operation, the operation for replacing the insides of the flow paths of the system reagent supply nozzles, the system reagent reservoirs and the washing reagent supply hole of the reagent nozzle washing tank with the system reagents and the operation for disposing of the reaction containers 105 which remain on the incubator disk 104 and in the stirring mechanism 108, which take a long time, are skipped. Alternatively, the operation for replacing the insides of the flow paths of the system reagent supply nozzles, the system reagent reservoirs and the washing reagent supply hole of the reagent nozzle washing tank with the system reagents may be replaced with a simplified system reagent supply operation which can be carried out in a shorter time.

On the other hand, when the possibility of a malfunction during the starting processing of the analyzer or access by the operator to the analysis unit after the starting processing of the analyzer is detected, it is decided that the conditions of the system reagents in the system reagent dispensing nozzles and the system reagent reservoirs and the reaction containers 105 on the incubator disk 104 and on the stirring mechanism 108 are uncertain, and all of the items of the analysis preparation operation are carried out. In this regard, as means for detecting the possibility of access by the operator to the analysis unit, for example, a sensor which detects the state of opening and closing is provided on the top cover of the analysis unit, and the condition detected by the sensor is monitored.

In this regard, examples of the case where the operator accesses the analysis unit after the starting processing of the analyzer are the operation for cleaning the parts of the analysis unit such as the sample dispensing nozzle 103 and the reagent dispensing nozzle 114, the operation for setting the washing solution into the analysis unit for carrying out the maintenance for washing the flow paths as well as the reaction solution suction nozzle 115 and the detection unit 116 and the like.

When there has been no malfunction during the starting processing of the analyzer but a maintenance item including the operation for replacing the system reagents in the flow paths of the system reagent supply nozzles, the system reagent reservoirs or the washing reagent supply hole of the reagent nozzle washing tank with water has been carried out after the starting processing of the analyzer, it is decided that the insides of the flow paths of the system reagent supply nozzles, the system reagent reservoirs or the washing reagent supply hole of the reagent nozzle washing tank have been replaced with water and that no reaction container 105 remains on the incubator disk 104 and in the stirring mechanism 108. Then, of the items of the analysis preparation operation, only the disposal of the reaction containers which remain on the incubator disk 104 and in the stirring mechanism 108 is skipped.

In this regard, examples of the maintenance item including the operation for replacing the system reagents in the flow paths of the system reagent supply nozzles, the system reagent reservoirs or the washing reagent supply hole of the reagent nozzle washing tank with water are the maintenance for washing the flow paths including the reaction solution suction nozzle 115 and the detection unit 116, the maintenance for changing the detection sensor of the detection unit 116 and the like.

When there has been no malfunction during the starting processing of the analyzer but the system reagent bottles have been changed after the starting processing of the analyzer, it is decided that it is necessary to fill the flow paths of the system reagent supply nozzles, the system reagent reservoirs and the washing reagent supply hole of the reagent nozzle washing tank with new system reagents and that no reaction container 105 remains on the incubator disk 104 and in the stirring mechanism 108. Then, of the items of the analysis preparation operation, only the disposal of the reaction containers which remain on the incubator disk 104 and in the stirring mechanism 108 is skipped.

In the second analysis after starting the analyzer or in the analysis after the second analysis, based on the monitoring results of presence or absence of a malfunction during the last analysis, the maintenance item which has been carried out after the last analysis, presence or absence of access by the operator to the analysis unit and presence or absence of change of the system reagent bottles, the analysis preparation operation is selected and carried out.

When there has been no malfunction during the last analysis, no maintenance carried out after the last analysis, no access by the operator to the analysis unit and no change of the system reagent bottles, it is decided that the insides of the flow paths of the system reagent supply nozzles, the system reagent reservoirs and the washing reagent supply hole of the reagent nozzle washing tank have already been replaced with the system reagents and that no reaction container 105 remains on the incubator disk 104 and in the stirring mechanism 108. Then, from the analysis preparation operation, the replacement of the insides of the flow paths of the system reagent supply nozzles and the system reagent reservoirs with the system reagents and the disposal of the reaction containers 105 which remain on the incubator disk 104 and in the stirring mechanism 108, which take a long time, are skipped. Alternatively, the operation for replacing the insides of the flow paths of the system reagent supply nozzles, the system reagent reservoirs and the washing reagent supply hole of the reagent nozzle washing tank with the system reagents may be replaced with a simplified system reagent supply operation which can be carried out in a shorter time.

On the other hand, when the possibility of a malfunction during the last analysis or access by the operator to the analysis unit after the starting processing of the analyzer is detected, it is decided that the conditions of the system reagents in the system reagent dispensing nozzles and the system reagent reservoirs and the reaction containers 105 on the incubator disk 104 and on the stirring mechanism 108 are uncertain, and all of the items of the analysis preparation operation are carried out.

When there has been no malfunction during the last analysis but a maintenance item including the operation for replacing the system reagents in the flow paths of the system reagent supply nozzles, the system reagent reservoirs and the washing reagent supply hole of the reagent nozzle washing tank with water has been carried out after the last analysis, it is decided that the insides of the flow paths of the system reagent supply nozzles, the system reagent reservoirs and the washing reagent supply hole of the reagent nozzle washing tank have been replaced with water and that no reaction container 105 remains on the incubator disk 104 and in the stirring mechanism 108. Then, of the items of the analysis preparation operation, only the disposal of the reaction containers which remain on the incubator disk 104 and in the stirring mechanism 108 is skipped.

When there has been no malfunction during the starting processing of the analyzer but the system reagent bottles have been changed after the starting processing of the analyzer, it is decided that it is necessary to fill the flow paths of the system reagent supply nozzles, the system reagent reservoirs and the washing reagent supply hole of the reagent nozzle washing tank with new system reagents and that no reaction container 105 remains on the incubator disk 104 and in the stirring mechanism 108. Then, of the items of the analysis preparation operation, only the disposal of the reaction containers which remain on the incubator disk 104 and in the stirring mechanism 108 is skipped.

After finishing the analysis, the operation for replacing the system reagents in the flow paths of the system reagent supply nozzles, the system reagent reservoirs and the washing reagent supply hole of the reagent nozzle washing tank with water is skipped from the items constituting the analysis-ending operation, and the operation for disposing of the reaction containers 105 which remain on the incubator disk 104 and in the stirring mechanism 108 is mainly carried out. As a result, the flow paths of the system reagent supply nozzles, the system reagent reservoirs and the washing reagent supply hole of the reagent nozzle washing tank keep the state of containing the system reagents.

However, when the interval between the starting processing of the analyzer or the last analysis and the resumption of the analysis is long, there is a possibility of the precipitation of crystals due to the evaporation and the concentration of the reagents in the system reagent supply nozzles, the system reagent reservoirs and the washing reagent supply hole of the reagent nozzle washing tank. Therefore, regular automatic supply of the system reagents or optimization of the system reagent replacement operation and the amounts of the supplied system reagents in the analysis resumption preparation operation according to the time until the resumption of the analysis is preferably carried out.

When the analyzer is shut down, after first carrying out the analyzer-ending operation in response to the request for shutting down from the operator, shutting down (turning off of the power supply) is carried out. As the analyzer-ending operation, the operation for replacing the system reagents in the flow paths of the system reagent supply nozzles and the system reagent reservoirs and the inside of the washing reagent supply hole of the reagent nozzle washing tank with water is carried out. This is for preventing the precipitation of crystals due to the evaporation and the concentration of the reagents in the system reagent supply nozzles, the system reagent reservoirs and the washing reagent supply hole of the reagent nozzle washing tank while the analyzer is not in operation. In this regard, in the normal analysis mode, which carries out the entire analysis-ending operation and analysis preparation operation, the analyzer-ending operation does not have to be carried out upon the request for shutting down.

(5) Effects

The effects of the embodiment which is constituted as described above are explained.

In an automatic analyzer, the reliability of the analysis results is improved and the accuracy of the analysis is stabilized by appropriately managing the condition of the analyzer according to circumstances, for example by carrying out a preparation operation for bringing the condition of the analyzer into suitable condition for the analysis before the analysis operation, carrying out an ending operation for bringing the analyzer into proper standby condition after the analysis operation and the like.

Here, the operations which are carried out before and after the analysis operation are related to the increase and the decrease in the TAT (Turn Around Time). Accordingly, for the purpose of shortening the TAT, a conventional technique and the like in which it is selected whether a designated preparation operation of the analysis preparation processes which are necessary before starting the analysis with the automatic analyzer is carried out during the initial processing for starting up the power supply of the analyzer or after starting the analysis have been disclosed. However, in the conventional technique, by carrying out a designated preparation operation of the analysis preparation processes of the automatic analyzer during the initial processing for starting up the power supply of the analyzer, the period between the point at which the request for analysis is made and the point at which the analysis is actually started is shortened. Thus, the reduction in the TAT is just restricted to the measurement soon after starting the analysis, and the technique has room for further improvement.

On the other hand, the embodiment is constituted in such a manner that one or more ending operation items to be carried out are determined from the ending operation items which are set as the analysis-ending operation which is carried out when ending the analysis operation for analyzing the sample to be analyzed and that one or more preparation operation items to be carried out are determined from the preparation operation items which are set as the analysis preparation operation based on the monitoring results of the condition of the automatic analyzer between the completion of the analysis-ending operation and the start of the analysis preparation operation for preparing for the analysis operation. Thus, the time required for the analytical processing can be shortened by making the operations related to the analytical processing more efficient.

REFERENCE SIGNS LIST

100 Analyzer
101 Rack
102 Sample container
103 Sample dispensing nozzle
104 Incubator disk
105 Reaction container
106 Sample dispensing tip- and reaction container-carrying mechanism
107 Sample dispensing tip- and reaction container-holding member
108 Stirring mechanism
109 Sample dispensing tip- and reaction container-disposal hole
110 Sample dispensing tip-attaching position
111 Reagent disk
112 Reagent disk cover
113 Reagent disk cover opening
114 Reagent dispensing nozzle
115 Reaction solution suction nozzle
116 Detection unit
117 Rack-carrying line
118 Reagent container
119 Control unit 121 Reagent probe washing tank
122 washing reagent supply hole
123 Reaction auxiliary reagent reservoir
124 Reaction auxiliary reagent supply nozzle
125 Washing reagent reservoir
126 Washing reagent supply nozzle
127 Top cover opening/closing detection sensor
130 Input unit
131 Memory unit
132 Operation unit
133 Output unit
140 Analysis mode selection screen
151 Reaction auxiliary reagent syringe
152 Washing reagent syringe
153 Reaction auxiliary reagent bottle
154 Washing reagent bottle
155 Waste liquid receiver
156 Changeover valve (reaction auxiliary reagent syringe)
157 Changeover valve (washing reagent supply nozzle)
158 Changeover valve (reaction auxiliary reagent supply nozzle)
159 Changeover valve (reaction auxiliary reagent bottle)
160 Changeover valve (waste reaction auxiliary reagent)
161 Changeover valve (washing reagent bottle)
162 Changeover valve (reagent nozzle washing)
163 Changeover valve (waste washing reagent)
164 Changeover valve (washing reagent syringe)

The invention claimed is:

1. A method for controlling an automatic analyzer, comprising the steps of:
   selecting a mode, which is one of a normal mode for carrying out analysis preparation operation items, in an analysis preparation operation, which are set in advance, and a time-saving mode for carrying out fewer analysis preparation operation items than in the normal mode;
   monitoring one or more conditions of the analyzer between a completion of a startup processing of the automatic analyzer and a start of an analysis preparation operation for preparing for an analysis operation and between a completion of an analysis-ending operation and the start of the analysis preparation operation for preparing for the analysis operation;
   determining one or more analysis preparation operation items to be carried out from the analysis preparation operation items set as the analysis preparation operation based on the selected operation mode and on the monitoring result of the one or more conditions of the automatic analyzer; and
   performing the analysis preparation operation based on the determined one or more analysis preparation operation items.

2. The method for controlling an automatic analyzer according to claim 1,
   wherein the one or more monitored conditions of the automatic analyzer include at least one of presence or absence of a malfunction which occurs during startup of the automatic analyzer, presence or absence of a malfunction during the analysis operation, presence or absence of access by the operator to an analysis unit between the completion of the analysis operation and the start of the analysis preparation operation, presence or absence of maintenance which is carried out between the completion of the analysis operation and the start of the analysis preparation operation, type of the maintenance carried out, a presence or absence of a change of a reagent used for the analysis, the elapsed time since the completion of the startup processing of the automatic analyzer or the completion of the last analysis and the elapsed time since maintenance of a system reagent.

3. The method for controlling an automatic analyzer according to claim 1,
   wherein the analysis preparation operation items of the analysis preparation operation include at least one of an operation item of filling a reagent supply flow path for supplying a reagent used for the analysis with the reagent and an operation item of disposing of a reaction container used for the analysis operation.

4. The method for controlling an automatic analyzer according to claim 1,
   wherein the one or more monitored conditions of the automatic analyzer includes presence or absence of replacement of a reagent used for the analysis in a reagent supply flow path for supplying the reagent with water, wherein the presence or the absence is decided based on type of maintenance which is carried out.

5. The method for controlling an automatic analyzer according to claim 1,
   further comprising wherein a step of determining one or more ending operation items to be carried out from ending operation items set as the analysis-ending operation which is carried out when ending the analysis operation based on the set operation mode.

* * * * *